(12) United States Patent
Malucelli et al.

(10) Patent No.: US 7,429,130 B2
(45) Date of Patent: Sep. 30, 2008

(54) UNIT FOR ACQUIRING DENTAL RADIOGRAPHIC IMAGES

(75) Inventors: Stefano Malucelli, Cannuzzo Di Cervia (IT); Eros Nanni, Castel Guelfo Di Bologna (IT)

(73) Assignee: CEFLA Societa Cooperative (IT)

( * ) Notice: Subject to any disclaimer, the term of this patent is extended or adjusted under 35 U.S.C. 154(b) by 0 days.

(21) Appl. No.: 11/604,651

(22) Filed: Nov. 27, 2006

(65) Prior Publication Data
US 2007/0237292 A1  Oct. 11, 2007

(30) Foreign Application Priority Data
Nov. 28, 2005 (IT) .......................... BO2005A0721

(51) Int. Cl.
*H05G 1/02* (2006.01)
(52) U.S. Cl. ........................................ 378/197; 378/38

(58) Field of Classification Search ............. 378/38–40, 378/193–197; 248/278.1; 403/83, 84
See application file for complete search history.

(56) References Cited

U.S. PATENT DOCUMENTS

| 4,548,373 | A | | 10/1985 | Komura |
| D290,500 | S | * | 6/1987 | Makas et al. ............... D24/158 |
| 5,820,555 | A | | 10/1998 | Watkins, III et al. |
| D469,182 | S | * | 1/2003 | Choi et al. ................. D24/158 |
| 6,837,468 | B1 | | 1/2005 | Kantor et al. |
| 2004/0104328 | A1 | | 6/2004 | Frick |

FOREIGN PATENT DOCUMENTS

| CH | 474265 | 6/1969 |
| EP | 1520548 | 4/2005 |

* cited by examiner

*Primary Examiner*—Courtney Thomas
(74) *Attorney, Agent, or Firm*—Lieberman & Brandsdorfer, LLC

(57) ABSTRACT

In a unit for acquiring dental radiographic images of a patient, an X-ray head is connected to a supporting device by at least one cylindrical joint having a pin fitted inside a hub defined by two tightening members, which extend about the pin and are movable with respect to each other to and from a lock position locking the pin.

4 Claims, 2 Drawing Sheets

UNIT FOR ACQUIRING DENTAL RADIOGRAPHIC IMAGES

The present invention relates to a unit for acquiring dental radiographic images.

BACKGROUND OF THE INVENTION

In dentistry, a unit for acquiring dental radiographic images is known comprising an X-ray head for emitting X-rays; at least one supporting arm supporting the X-ray head; and connecting means connecting the X-ray head to the supporting arm.

The connecting means normally comprise a connecting bracket hinged to the X-ray head and the supporting arm by two cylindrical joints to rotate, with respect to the X-ray head and the supporting arm, about respective hinge axes substantially crosswise to each other.

Each cylindrical joint comprises a hub; and a pin fitted in rotary manner in, and connected frictionally to, the hub.

Known units for acquiring dental radiographic images of the above type have various drawbacks, mainly due to the friction connection of the pins to the relative hubs, which, on the one hand, makes the X-ray head fairly hard to move about the hinge axes, and, on the other, once the X-ray head is set to the correct position, fails to ensure the correct position is maintained.

SUMMARY OF THE INVENTION

It is an object of the present invention to provide a unit for acquiring dental radiographic images, designed to eliminate the aforementioned drawbacks, and which is cheap and easy to produce.

According to the present invention, there is provided a unit for acquiring dental radiographic images, as claimed in the attached Claims.

BRIEF DESCRIPTION OF THE DRAWINGS

A non-limiting embodiment of the present invention will be described by way of example with reference to the accompanying drawings, in which.

DETAILED DESCRIPTION OF THE INVENTION

Figure 1:
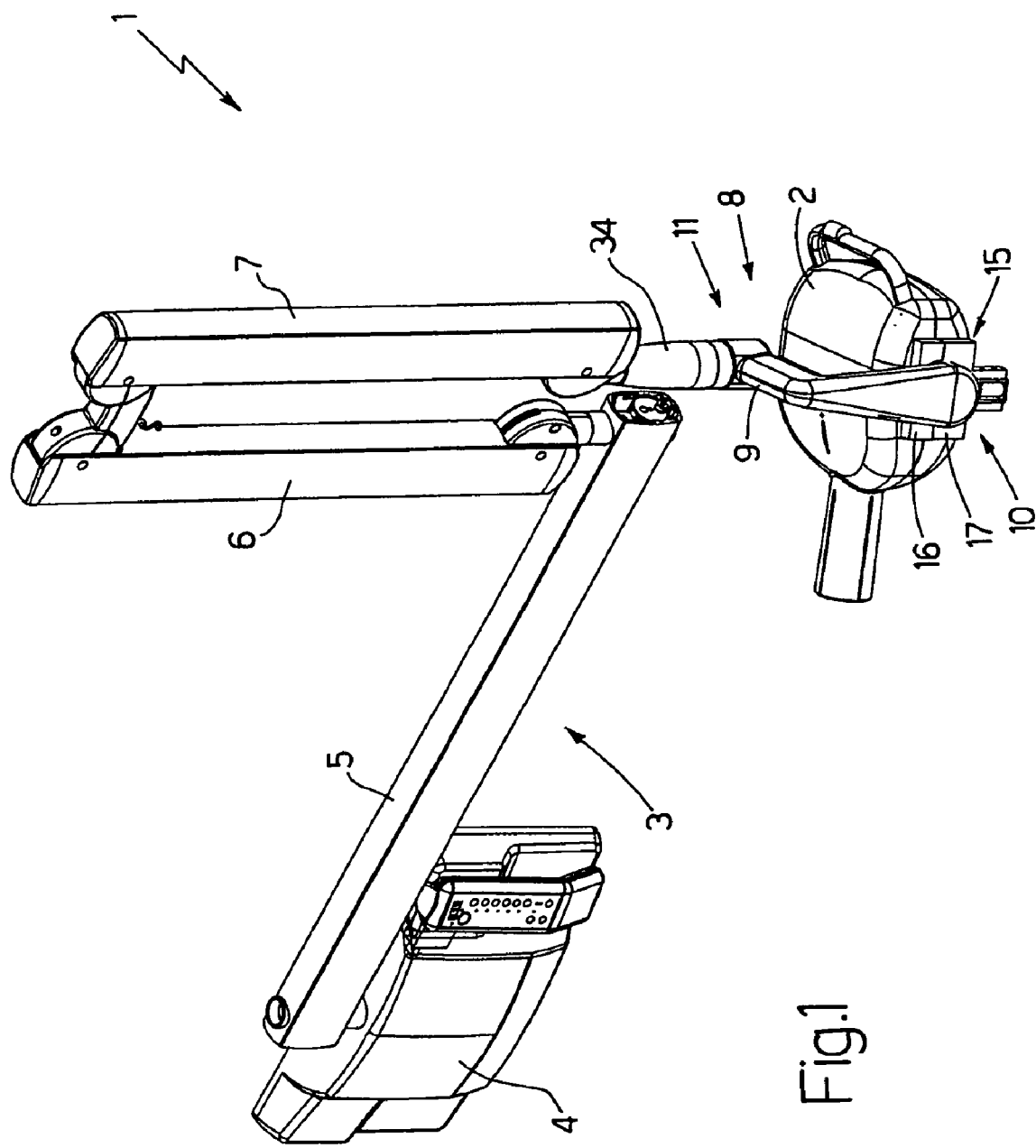
FIG. 1 shows a schematic view in perspective of a preferred embodiment of the unit according to the present invention.
Figure 2:
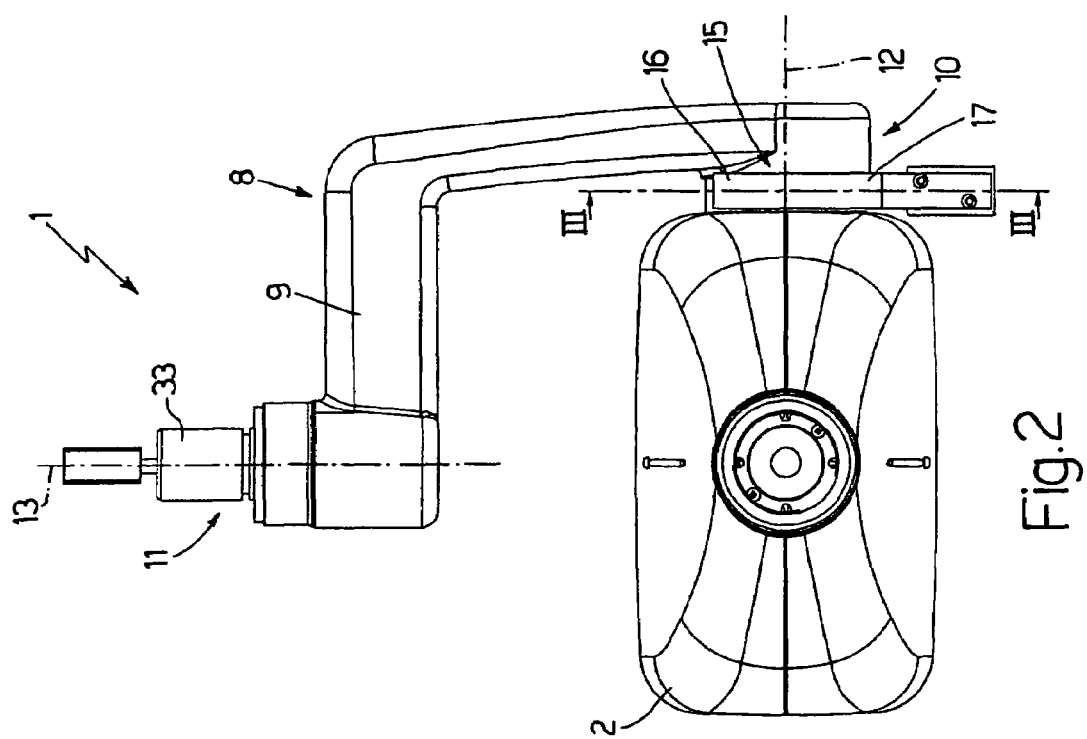
FIG. 2 shows a schematic side view of a detail of the FIG. 1 unit.

Number 1 in FIGS. 1 and 2 indicates as a whole a unit for acquiring dental radiographic images of a patient (not shown)—in the example shown, a wall-mounted unit fitted to a wall (not shown) of a dental surgery.

In a variation not shown, unit 1 is mounted on a dental surgery instrument unit.

Unit 1 comprises an X-ray head 2 for emitting X-rays; and a supporting device 3 supporting X-ray head 2 and in turn comprising a box-shaped body 4 by which to fix unit 1 to the wall (not shown) of the dental surgery, a horizontal arm 5 connected in rotary manner to body 4, and two articulated supporting arms 6, 7, of which arm 6 is connected in rotary manner to arm 5, and arm 7 is connected in rotary manner to arm 6.

Head 2 is connected to arm 7 by a connecting device 8 comprising a substantially L-shaped bracket 9 connected to head 2 and to arm 7 by respective cylindrical joints 10, 11 to rotate, with respect to head 2 and arm 7, about respective hinge axes 12, 13 substantially crosswise to each other.

Figure 3:
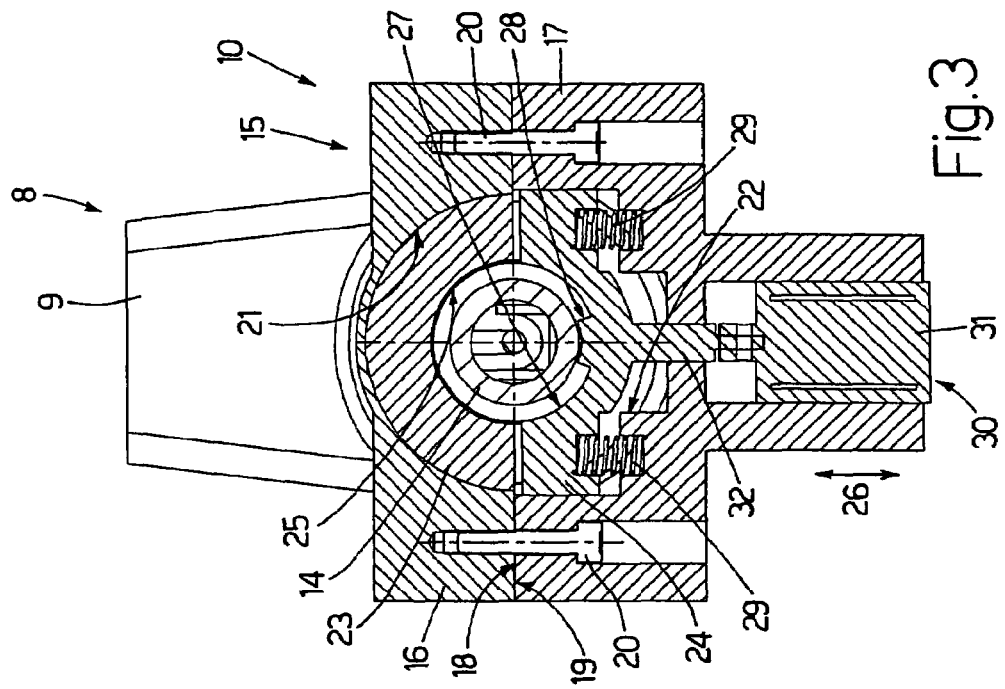
FIG. 3 shows a section along line III-III in FIG. 2.

As shown in FIG. 3, joint 10 comprises a pin 14, which projects from head 2, coaxially with axis 12, and engages in rotary manner a hub 15 supported by bracket 9 and in turn comprising two plates 16, 17, which are positioned contacting each other at respective substantially flat surfaces 18, 19 parallel to axis 12, and are fixed to each other by lock screws 20.

In each of plates 16, 17 is formed a seat 21, 22, which faces the other seat 22, 21, opens outwards at relative surface 18, 19, and houses a relative tightening member 23, 24.

Member 23 is fixed inside seat 21, and is bounded internally by a substantially semicylindrical surface 25 extending about pin 14, coaxially with axis 12; whereas member 24 is fitted in sliding manner inside seat 22 to slide, with respect to seat 22 and therefore to member 23, in a direction 26 perpendicular to surfaces 18, 19 and crosswise to axis 12. Member 24 is bounded internally by a substantially semicylindrical surface 27, which extends about pin 14 and has, in the example shown, a tooth 28 projecting radially from surface 27 towards pin 14.

Member 24 is normally maintained in a lock position—in which tooth 28 contacts pin 14 to lock head 2 in a given angular position about axis 12—by two springs 29 substantially parallel to direction 26 and interposed between plate 17 and member 24.

Member 24 is moved, in opposition to springs 29, from the lock position to a release position—in which tooth 28 is positioned a given distance from pin 14 to allow head 2 to rotate about axis 12—by an actuating device 30 comprising a selectively excitable electromagnet 31 positioned facing a stem 32 projecting in direction 26 from member 24 and on the opposite side to tooth 28.

In actual use, when electromagnet 31 is excited to move member 24 in direction 26 into the release position in opposition to springs 29, pin 14 and therefore head 2 are free to rotate about axis 12. Once head 2 is set to a given angular position about axis 12, electromagnet 31 is deactivated to allow springs 29 to move member 24 back into the lock position locking pin 14 and therefore head 2 about axis 12.

In the example shown in FIGS. 1, 2 and 3, joint 11 is a conventional type comprising a pin 33, which is supported by bracket 9, engages in rotary manner a hub 34 supported by arm 7, and is locked frictionally inside hub 34.

In a variation not shown, joint 11 is designed the same way as joint 10.

The invention claimed is:

1. A unit for acquiring dental radiographic images of a patient, comprising an X-ray head (2); supporting means (3) supporting the X-ray head (2); and connecting means (8) connecting the X-ray head (2) to said supporting means (3); the connecting means (8) comprising at least one cylindrical joint (10, 11), in turn comprising a hub (15) and a pin (14) fitted inside the hub (15); and the unit being characterized in that the hub (15) comprises two tightening members (23, 24), which extend about said pin (14) and are movable with respect to each other to and from a lock position locking the pin (14); actuating means (29, 30) being provided to move the tightening members (23, 24) between said lock position and a release position.

2. A unit as claimed in claim 1, wherein said actuating means (29, 30) comprise first actuating means (29) for moving the tightening members (23, 24) from said release position to said lock position; and second actuating means (30) for moving the tightening members (23, 24) from said lock position to said release position.

3. A unit as claimed in claim 2, wherein said first actuating means (29) are elastic actuating means, which normally maintain the tightening members (23, 24) in said lock position.

4. A unit as claimed in claim 1, wherein at least one of said tightening members (23, 24) has at least one tooth (28) projecting radially from an inner surface (27) of the tightening member (23, 24) towards the pin (14), and which engages the pin (14) when the tightening members (23, 24) move from the release position to the lock position.

\* \* \* \* \*